United States Patent [19]

Midgley et al.

[11] Patent Number: 5,278,080
[45] Date of Patent: Jan. 11, 1994

[54] METHOD FOR MEASURING THE FREE FRACTION OF LIGANDS IN BIOLOGICAL FLUIDS

[75] Inventors: John E. Midgley, Great Missenden; Christopher P. Sheehan; Nicos D. Christofides, both of Cardiff, all of England

[73] Assignee: Amersham International PLC, Buckinghamshire, Great Britain

[21] Appl. No.: 22,416

[22] Filed: Feb. 11, 1993

Related U.S. Application Data

[63] Continuation of Ser. No. 885,070, May 18, 1992, abandoned, which is a continuation of Ser. No. 551,580, Jul. 2, 1990, abandoned, which is a continuation-in-part of Ser. No. 473,964, Apr. 17, 1990, abandoned.

[51] Int. Cl.$^5$ .................. G01N 33/53; G01N 33/566; G01N 33/567; C12Q 1/00
[52] U.S. Cl. .................. 436/500; 436/501; 436/504; 435/7.1; 435/7.93
[58] Field of Search .......... 435/7.1, 7.9-93; 436/500-504

[56] References Cited

U.S. PATENT DOCUMENTS 4,292,296  9/1981  Parsons, Jr. .............................. 424/1
4,366,143  12/1982  Midgley et al. ...................... 436/501

FOREIGN PATENT DOCUMENTS 0303284  2/1989  European Pat. Off. .
8303306  9/1983  United Kingdom ........ G01N 33/54

*Primary Examiner*—Christine M. Nucker
*Assistant Examiner*—Jeffrey Stucker
*Attorney, Agent, or Firm*—Wenderoth, Lind & Ponack

[57] ABSTRACT

A one-step assay for the free portion of a ligand in a biological sample involves incubating a mixture of the sample with a labelled antibody for the ligand and a ligand analogue which competes with the ligand for binding to the antibody. The assay is characterized by choosing a ligand analogue which has a lower affinity for the antibody than does the ligand. An insolubilised ligand analogue preferably has a binding affinity for the antibody from 0.01% to 10% of that of the ligand. Ligand/ligand analogue pairs exemplified are T4/T3 (Thyroxine/Tri- iodothyronine); Testosterone/etiocholanol; and T3/T2.

9 Claims, 3 Drawing Sheets

METHOD FOR MEASURING THE FREE FRACTION OF LIGANDS IN BIOLOGICAL FLUIDS

This application is a continuation of now abandoned application Ser. No. 07/885,070 filed on May 18, 1992 which is a continuation of now abandoned application Ser. No. 07/551,580 filed on Jul. 2, 1990, which is a continuation-in-part of Ser. No. 07/473,964 filed on Apr. 17, 1990 now abandoned which is the U.S. national stage of International Application No. PCT/GB89/00003, filed Jan. 5, 1989.

This invention relates to specific binding assays for the free fraction of organic substances or ligands in biological fluids, where the organic substances or ligands are also bound to protein (or other binding species) present in the fluids in equilibrium with the free fraction. In particular, this invention relates to the field of competitive ligand binding assays more specifically, it relates to the field of immunoassays used to determine the concentration of a non-protein-bound substance such as a hormone, a biochemical messenger, a steroid, a drug, a drug metabolite, a polypeptide or protein, a vitamin, a tumour antigen, a toxin, an alkaloid, a mono-, di- or polysaccharide in the presence of protein-bound forms of that substance in a biological fluid such as blood plasma or serum.

Many physiologically active ligands are found both in a free and a protein-bound form in biological fluids such as blood. The bound form probably serves as a carrier for the ligand, which can be dissociated by mass action to form the free ligand, as the latter is used up in physiological processes. Usually, for ligands of this kind, and especially in respect of the invention described here, only a small percentage of the ligand is in the free form. Thus, since it is currently believed that the concentration of the free ligand is responsible for the control of physiological processes associated with these substances, rather than the total (which includes both the major bound and minor free fractions) it may be more valuable diagnostically to measure the free fraction as an indication of physiological activity.

A specific example of this concept is given by the role of thyroid hormones and their associated binding proteins in determining thyroid activity and clinical status in thyroid disease. For thyroxine, about 99.98% of the total hormone in the circulation is in a protein-bound state, and for the accompanying hormone triiodothyronine, about 99.7% is similarly protein-bound. Three naturally occurring proteins in blood serum or plasma will bind thyroxine and triiodothyronine, accounting for virtually all the protein-bound hormones: these are thyroxine-binding globulin (TBG), thyroxine-binding prealbumin (transthyretin, TBPA) and albumin (A). Nevertheless, it is now recognized that the severity of thyroid dysfunction is better correlated with the free thyroid hormone concentration than with the total or protein-bound concentration. Additionally, conditions such as estrogen therapy or pregnancy can lead to changes in the concentration of some or all of the thyroid hormone-binding proteins without a parallel significant effect on the free hormone concentrations. This is because the concentration of total (largely protein-bound) thyroid hormones changes in concert with the changes in thyroid hormone-binding proteins so as to maintain a constant free thyroid hormone concentration, through mass action effects.

A second example of the importance of the general concept is given by the role of the steroid hormone testosterone which is involved in the control of sexual and reproductive activity in man. Testosterone is found in blood plasma and serum both in a free form (approximately 2% of the total) and also bound (approximately 98%) to the naturally occuring plasma proteins sex hormone binding globulin (SHBG) and albumin (A). It is currently thought that it is the unbound (free) concentration of testosterone that regulates the pituitary-gonadal axis in healthy individuals. In this regard, promotion of measurements of "free testosterone" in saliva has been made, since it is believed that the salivary gland extracts only a measure of the free fraction of testosterone in blood, and thus gives more accurate clinical evaluation of the status of the patient. In addition, saliva does not contain significant amounts of SHBG so that direct measurement of testosterone in saliva is deemed to be a fairly accurate estimate of the unbound (free) fraction of the hormone in blood. Similar arguments may apply to the regulatory importance of other steroid hormones involved in the gonadal-pituitary axis, such as oestradiol and progesterone, where a high proportion of the hormones (>90%) is protein-bound to SHBG and albumin in blood plasma or serum. Further, in the case of cortisol, a steroid hormone involved in the regulation of the adrenal-pituitary axis, more than 90% of the hormone is bound to the major cortisol-binding protein transcortin and to albumin in blood serum or plasma. Also, it is believed that it is the free (approximately 8%) fraction of cortisol that is most important in physiological regulation rather than the total (bound+free) concentration. Again, measurements of salivary cortisol have been promoted as more accurate estimates of the free (unbound) fraction of cortisol in blood, since transcortin is not secreted in the saliva, and a measure of the salivary cortisol is thus related to the free plasma cortisol.

Classical methods for the measurement of the free fraction or concentration of a substance in the presence of protein-bound material involve the use of equilibrium dialysis or ultrafiltration. These methods, which both give reasonably accurate estimates of the concentration of the free fraction of most substances in most circumstances are often used for calibration or research purposes, but are generally too slow for routine use or are methodologically tedious as well as requiring expert handling. Accordingly, there has been pressure for the development of technically simpler methods to permit the routine measurement of free fractions of analytes of clinical interest in the clinical chemistry or pathology laboratory, where large numbers of samples need to be processed.

Several methods have been developed as convenient and simple techniques for measurement of free thyroid hormones in serum or plasma and are in current use in many laboratories. Direct ligand assays, more especially those for serum free thyroxine and free triiodothyronine, are characterized by the measurement of the free ligand itself, rather than by other methods which are correlated to the free ligand concentration by a calculation, such as the free thyroxine index. Virtually all direct free ligand assays rely on the fact that the removal of a negligibly small portion of the ligand in the equilibrium system in serum or plasma (defining the endogenous protein-bound and free ligand) for measurement by a specific ligand binder, such as an antibody, does not significantly alter the concentration of the free ligand that was present originally in the serum or plasma before the addition of the specific ligand binder. For the ligand thyroxine or triiodothyronine, less than 5% of the total available ligand (in protein-bound or free form) should be sequestered by the specific ligand binder. If more than 5% of the total ligand is sequestered by the specific ligand binder, then either the measurement of free ligand by direct interpolation of the assay dose-response curves may be compromised, or calculations have to be made to correct the altered free ligand concentration back to the concentration that existed before the specific ligand binder was added to the serum or plasma However, all methods are aimed at rendering the interference of variations in the concentrations of the ligand-binding proteins (and thus the protein-bound ligand concentrations) negligible with respect to the estimation of the free ligand The various methods so far developed differ in the way this aim is achieved.

In the method first developed commercially by Clinical Assays (GB 2030290), the endogenous protein binders of thyroxine in serum or plasma are prevented from interfering in the estimation of the free fraction of thyroxine by first incubating the serum or plasma in a tube whose inner surface is coated with the immobilized specific ligand binder (an antibody raised against, and specific for, thyroxine). Conditions are arranged so that a very small amount of thyroxine (considerably less than 5%) is sequestered by the specific ligand binder immobilized on the tube walls. This ensures that the removal of thyroxine from the serum equilibrium system of free and protein-bound ligand is small enough not to significantly affect the original endogenous equilibrium and thus the original free ligand concentration After a suitable incubation to allow a new equilibrium to be set up between the free ligand, the ligand bound by the endogenous protein binders and the specific ligand binder, the serum or plasma is separated by pouring off or aspiration, and a second incubation is performed in the tube with a prescribed amount of buffer containing radiolabelled thyroxine, when the binding sites of the specific ligand binder not already occupied by thyroxine from the first incubation are now occupied by the radiolabelled thyroxine. Since the fractional occupation of the binding sites of the specific ligand binder in the first incubation is proportional to the endogenous free ligand (thyroxine) concentration, the further occupation of otherwise vacant sites by radiolabelled thyroxine is inversely proportional to the original free ligand concentration. This method has the advantage that reagents well-known in the estimation of total thyroxine concentrations in serum or plasma can be used in this method of estimating the free ligand (thyroxine) concentration. It has however the disadvantage of requiring two sequential incubations to achieve the estimation, and may also be prone to the phenomenon of "drift", whereby in the second incubation, some degree of replacement of bound unlabelled ligand from the first incubation by radiolabelled ligand in the second incubation can occur, and affect the results.

Another method of direct free ligand assay is described in European patent 0 026 103 (Amersham International Plc). In this technique, the effects of the endogenous ligand binders in serum or plasma are neutralised by using a chemically modified derivative of the ligand (an "analogue" of the ligand) which has the joint properties of retaining its reactivity and binding to a very avid specific ligand binder (in competition with the free ligand) whilst having severely attenuated binding to the endogenous protein ligand binders in serum or plasma. Thus, rather than physically excluding the influence on ligand binding by the endogenous ligand binding proteins in serum or plasma, using separation techniques, the method uses differential chemical specificity to prevent their influence. This method has the advantage of technical convenience over the previous method, in that only one incubation is required in the assay, and the basic technique is typical of the usual one-step competitive ligand immunoassay methods well-known in the art of ligand analysis. The affinity of the ligand analogue tracer for the specific ligand binder need not be as great as that of the free ligand to be measured: indeed Wilkins, Midgley & Giles (1982) have taught that there is a correlation between the affinity constant of the specific ligand binder for the ligand analogue, and the amounts of specific ligand binder and ligand analogue required for an optimized assay for the free ligand. However, whatever the exact values for these parameters, the requirement for high avidity of the specific ligand binder for the ligand is absolute, and it is extremely important to minimize as far as possible the degree of residual binding of the ligand analogue to the endogenous ligand binders in serum or plasma. Otherwise, the measurement of free ligand by this technique is affected by changes in the concentration of any endogenous binder to which the analogue binds inappropriately strongly, and rather than being completely independent of the concentration of such endogenous binders, the assay will show some degree of correlation. Present assays for free thyroxine and free triiodothyronine developed using this technique have been successful in respect of their independence of variations in endogenous concentrations of TBG and TBPA, but it has proved more difficult to achieve sufficiently reduced affinity of the analogue of thyroxine for albumin binding sites to avoid some weak correlation of free thyroxine assay values with serum albumin concentration. Additionally, the assay is affected by thyroxine-specific autoantibodies that occur rarely in high concentration and with high avidity in some sera, since these antibodies can sequester the thyroxine analogue strongly, and remove it from the assay. Finally, the method requires the synthesis of specifically designed tracer analogues suitable for the measurement of each free analyte, posing in each case new chemical challenges in the development of tracers with the necessary characteristics of similarity to the corresponding analyte, reactivity with the analyte-specific ligand binder and essential nonreactivity with the endogenous binding proteins in serum or plasma.

EPA 89806 describes a competition assay which is generally similar except that the specific binder is labelled and the analyte derivative in immobilised.

To simplify reagent preparation in such assays, the technique described in Ekins (WO 83/03306) has been described. In this method, it is the specific ligand binder (the antibody) that is labelled as a tracer. The antibody can be labelled as an assay tracer with 125-I, or by conjugation with an active enzyme, a fluorescent or a chemiluminescent molecule. In the assay reaction, the free analyte in serum or plasma competes with an immobilised, or otherwise separable, unlabelled differential binding ligand analogue for binding with the labelled specific ligand binder. The technique is essentially an immunometric homologue of the direct immunoassay technique described in EP 0 026 103, except that in the former case, the analogue is labelled, whereas in the case described in WO 83/03306 the antibody is labelled. In both techniques, it is necessary that the analogue (labelled or unlabelled) binds comparatively weakly to the endogenous ligand binding proteins in serum or plasma. In WO 83/03306, it was considered necessary to purify ligand-specific polyclonal antibodies before labelling them with 125-I atoms. In addition, according to the patent applications and additional writings by its author, it is necessary (in an assay for free thyroxine) to use antibodies of a well-defined, suitably high avidity (association constant about $10^{11}$ L/mole) This requirement was conceived because the working of the assay was assumed to be a true equilibrium of ligand distributed between its free form, ligand bound to the endogenous ligand binders in serum or plasma, and ligand bound (in competition with the differential binding ligand analogue) to the labelled antibody. Thus, the Mass Action term describing the distribution of the ligand bound to the antibody directed against thyroxine at equilibrium is in the form:

[FT4].Kab.Pab/(1+Kab[FT4])

where
[FT4]=the free ligand (thyroxine) concentration,
Kab=the association constant of the antibody for thyroxine, and
Pab=the concentration of the antibody.

Assumptions of the true equilibrium status of practical free ligand immunoassays, as a complete explanation of their working, impose severe restrictions on the binding affinity of the antibodies suitable for use in such assays. Because the concentration of free thyroxine is about $10^{-11}$ mole/L in the mid-euthyroid range of thyroid clinical status, the above term will vary most over changes in [FT4] from zero to hyperthyroid values of $5 \times 10^{11}$ mole/L if the value of Kab is close to $10^{11}$ L/mole Thus, the term Kab[FT4] will be close to unity in the midrange of the assay, and its variation from zero to 5 or more in hyperthyroid sera allows the dose-response curve for any assay to be optimally, but not unusably, sensitive. On the contrary, if the value Kab was much greater than $10^{11}$ L/mole (e.g. greater than $10^{12}$ L/mole) than magnitude of the term Kab[FT4] would be much greater than unity for all reasonable values for [FT4] and thus the unity term in the denominator of the equation above would be a negligible quantity throughout the dose-response curve, making the curve over-sensitive. Also, if the value of Kab was much less than $10^{11}$ L/mole (e.g. equal to or less than $10^{10}$ L/mole), the value of Kab[FT4] in the denominator of the above term would be small compared with unity for all reasonable values of [FT4], thus giving an insensitive dose-response curve. From these requirements, it further follows that, if the value of Kab for the differential binding ligand analogue is of the same order as the value for the free ligand itself, the concentration of Pab (the labelled specific ligand binder) and the differential binding ligand analogue must also both be close to $10^{-11}$ mole/L, since otherwise higher concentrations of the differential binding ligand analogue would compete too strongly against the available free ligand, giving an insensitive dose-response curve. Practically, therefore, the antibody has to be labelled to a high specific activity with the tracer substance. Since, in the case of an assay for free thyroxine, it is difficult to obtain antibodies of such high avidity from other than polyclonal sources, such a purification step has to be undertaken in order to effect a labelling of the thyroxine-specific antibodies to a sufficiently high specific activity, in sufficient amount and in sufficient purity so that a viable assay could be obtained. In addition, it may be difficult to label the antibody to the high specific activity required without detriment to its binding affinities for free ligand or the differential binding ligand analogue. For hormones, such as cortisol, which bind to their most avid serum binding proteins less strongly than does thyroxine to TBG, the demands on the affinity of the antibody for a free ligand assay are less stringent, and affinities of about $10^8$ L/mole may be adequate for a viable assay of good sensitivity. However, given the feasibility of this essential step in the described method, the technique has the advantage of simpler synthetic pathways for the production of tracers for a variety of free ligand assays, in that the labelling of the antibody may be performed by similar chemical techniques in each case. Additionally, there may also be advantages in convenience in the synthesis of various differential binding ligand analogues, which may be achieved by similar techniques of chemical conjugation of each analyte to a common matrix, when the conjugated ligand analyte will in each case be rendered non-reactive with the binding sites of the endogenous serum ligand binding proteins. The assay described in WO 83/03306 thus comprises the combination of the test sample, ligand antibody and unlabelled, differential binding ligand analogue, incubating the mixture to allow the free ligand in the test sample and the differential binding ligand analogue to compete for binding with the ligand antibody. The amount of specific ligand binder (antibody) bound to the differential binding ligand analogue is inversely correlated to the amount of free ligand present in the test sample.

In practice, in a polyclonal mixture of ligand-specific antibodies of varying affinities, it is likely that any weaker binding fractions will be purified from the antiserum by affinity column techniques much more easily than the more avidly binding antibody fractions (which are the species required for the successful performance of the above invention). Further, the design of the differential binding ligand analogue has to be considered carefully, given the possibility that residual binding activity of the endogenous serum ligand-binding proteins may occur with the differential binding ligand analogue. If a differential binding ligand analogue is used where the affinity of the endogenous serum ligand-binding proteins is small compared with the affinity of the antibody for the ligand residue in the differential binding ligand analogue, such potential interferences might well be reduced to negligible levels. It must be noted in this case that it may be an added advantage if both the endogenous serum ligand-binding proteins and the antibody have considerably attenuated affinity for the ligand residue in the differential binding ligand analogue, compared with the affinity of the antibody for the free ligand it is sought to measure. Several advantages then accrue to the system. Firstly, considerably more differential binding ligand analogue can be used compared with the amount of labelled antibody, giving more flexibility in devising a system with the ability to encompass a wide variety of sera with widely differing ligand-binding proteins concentrations and affinities for the ligand. Secondly, the general characteristics of the assay such as precision and dose-response sensitivity could be improved by this increased flexibility. Thirdly, any problems of assay "drift" that may arise from slow replacement of the ligand bound to the antibody by the differential binding ligand analogue can be minimized, if the analogue binds much less strongly to the antibody than to the ligand. To give a specific example, an immunometric free ligand assay, using as a differential binding ligand analogue a ligand residue that binds only weakly to the endogenous ligand binding proteins, could employ a sufficient quantity of differential binding ligand analogue to bind avid autoantibodies against the ligand (or indeed its cross-reactants) that occur in certain patients sera, without affecting the binding of the assay's antibody. In the case where the ligand residue in the differential binding ligand analogue was a species binding as strongly as, or more strongly than, the ligand to the endogenous ligand bind proteins or the antibody, then much less differential binding ligand analogue could be used, as otherwise virtually all the antibody would be bound to the analogue at the expense of binding the free ligand. Accordingly, the presence of additional avid autoantibodies for the ligand might then interfere strongly with the binding of the antibody. The use of differential binding ligand analogues with a relatively low affinity of the ligand analogue residue for both the endogenous ligand-binding proteins and the antibody thus minimizes the chance of interference in the assay for free ligand by the endogenous ligand-binding proteins, whether common or rare. If however, only the antibody had lowered affinity with the differential binding ligand analogue, the potential for interference by endogenous ligand-binding proteins would remain. Additionally, the use of a weak-binding ligand analogue in a differential binding analogue complex will minimize the possibility of displacement of the ligand bound to the endogenous binding proteins, even if such proteins were capable of interaction with the differential binding analogue complex itself. This again minimizes the chance of altering the measured free ligand concentration through a disturbance of the equilibrium between bound and free ligand.

In the present invention, the considerations described above in the design of the differential binding ligand analogue are combined with the use of a monoclonal or polyclonal antibody of sufficiently high affinity for the ligand to produce an assay for the free ligand concentration in serum or plasma. Use of a monoclonal antibody of suitable affinity for the ligand, which is preferred, greatly reduces the difficulty in WO 83/03306 of purifying antibodies of high affinity for the ligand from a polyclonal source, and the commensurate difficulty of producing sufficient antibody labelled to a suitably high specific activity. In addition, a monoclonal antibody preparation comprises a much more uniform collection of molecules as regards their affinity for the ligand than does a purified polyclonal preparation, where species of unsuitably low affinity for the ligand are highly likely to be present. Thus, effectively, the use of a weak differential binding ligand analogue as a receptor for that fraction of the antibody not occupied by the ligand itself acts as an enhancer of the avidity of the antibody for the ligand in the separation of ligand-bound and non-ligand-bound fractions.

The invention provides a method of assaying the free portion of a ligand in a biological fluid sample which also contains a portion of the ligand bound to one or more natural binders, by the use of a signal reagent which is an antibody for the ligand and of a differential-binding ligand analogue which competes with the ligand for binding to the antibody, which method comprises incubating the sample with the analogue and the antibody, and observing the extent of binding of the antibody to the analogue, characterized in that the analogue is chosen to have a lower affinity than the ligand for binding with the antibody.

The differential-binding ligand analogue should bind to the natural binders in the biological fluid, either not at all, or else much more weakly than does the ligand. This is a standard requirement for free ligand assays, and is the reason why the analogue is designated a "differential" ligand analogue. This ligand analogue may be a molecule which resembles the ligand, but this is not necessary. It may, for example, be an anti-idiotype antibody, as described in European patent 106615 (Amersham International plc). An essential requirement of the ligand analogue is that it binds to the antibody, either at the same or neighbouring sites as the ligand, and therefore competes with the ligand for binding to the antibody.

In order to further reduce its binding affinity, both for natural binders in the biological fluid and for the antibody, the analogue may be covalently bonded to a large molecule to form a differential-binding ligand analogue complex. This large molecule may be water-soluble or may be a solid matrix. Preferably, the analogue is insolubilised prior to the incubation step, for example by being covalently bonded to cellulose or polystyrene particles. It is possible to perform the incubation with the analogue in solution, but if the analogue is subsequently brought down out of solution, this must be done without displacing antibody bound to it.

The antibody may be labelled with any of the labels conventionally used in assays, for example luminescent, fluorescent and enzyme label systems, and particularly radioactive labels such as 125-I. Alternatively, the antibody to the ligand can be unlabelled, and use made of a labelled second antibody. This may permit use of a universal labelling reagent.

The binding affinity of the differential binding ligand analogue with the antibody is preferably from 0.01% to 10% of the binding affinity of the free ligand with the antibody. This invention permits the use of a rather high concentration of rather low affinity analogue, such that the ratio of the effective analogue concentration to the antibody concentration in the incubation mixture is preferably from 10 to $10^5$. An optimization procedure is needed, as with all such assays, taking account of the affinities and concentrations of the various reagents. It is preferred that the ratio a): b) is between 0.1 to 10, where a) is (the affinity constant of the antibody for the analogue times the effective concentration of the analogue), and b) is (the affinity constant of the antibody for the ligand times the concentration of ligand bound to antibody at the end of the incubation).

Preferably also, the concentration of analogue binding sites for antibody, and the free ligand concentration, are both substantially the same at the beginning and at the end of the incubation step. For example, any change in either concentration during the incubation step is likely to be less than 5%.

Reference is to the accompanying drawings, in which.

DESCRIPTION OF THE INVENTION

Figure 1:
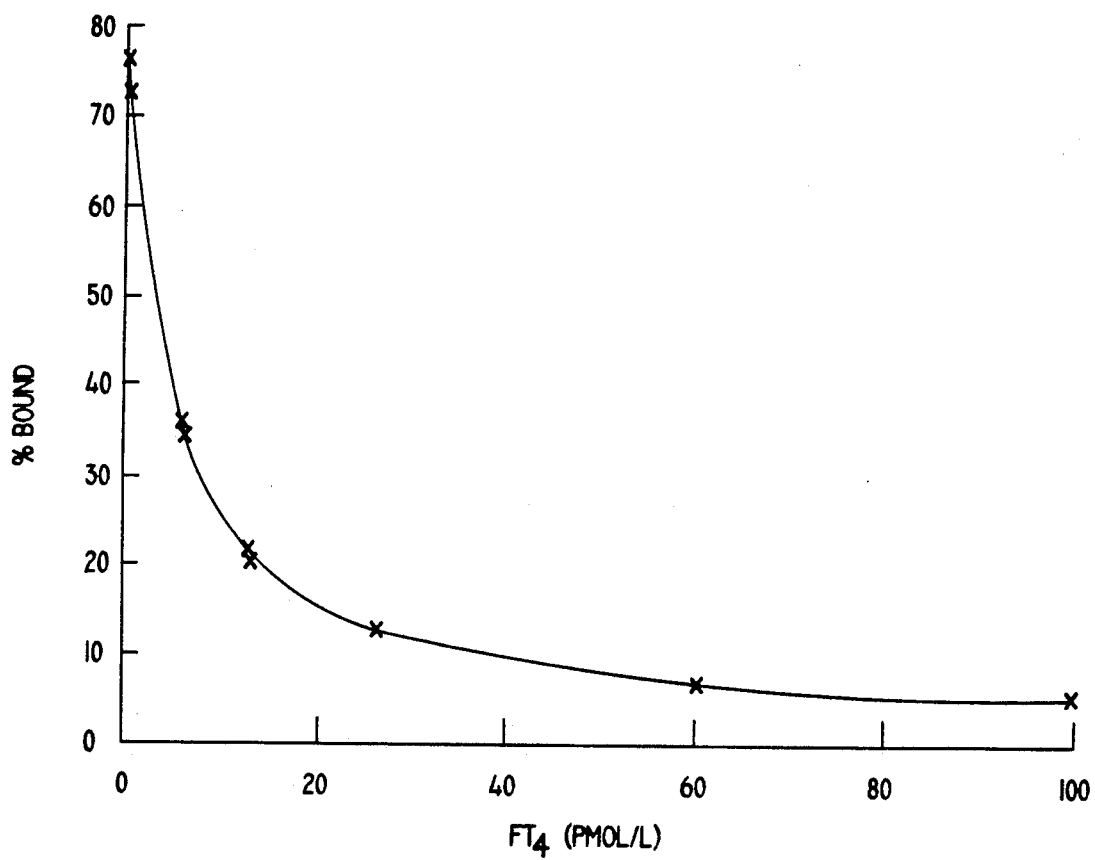
FIG. 1 is a typical dose-response curve generated in the free T4 assay described in detail below.

The production of suitable differential binding ligand analogues that retain binding affinity for antibodies but are essentially inactive with the endogenous ligand binding proteins in serum or plasma is well described in the art. Examples for standard immunoassay techniques are also given in EP 0 026 103 and references cited therein The ligand to be used in a corresponding immunometric free ligand assay can be modified in several ways to achieve the same aim. The charge or steric profile of the ligand can be altered to affect the affinity of the ligand for its endogenous binding receptors in serum or plasma, or ligands or ligand analogues can be used that are known to be both weak cross-reactants in the binding characteristics of the antibody and weaker binders to the endogenous binding receptors than the free ligand being measured in the assay. Such ligands or ligand analogues can be further inhibited from reaction with the endogenous binding proteins by substitution on to a large molecule such as a protein or synthetic or natural polymer. Thus, the already weakened binding of the ligand analogue to the endogenous binding receptors (compared with the free ligand being measured) is further reduced by the steric hindrance or charge interference caused by the bulky substitution. A further consideration to be made is that the ligand analogues should be attached to large molecules such that their residues are sterically available for binding with the antibody and yet not so exposed as to become available for binding with the unoccupied sites of the endogenous binding receptors. In this respect, the use of a weak ligand analogue as a part of the differential binding ligand analogue complex is an advantage, since larger quantities can be used, and so minor binding of the endogenous binding receptors can be tolerated, as they do not sensibly reduce the number of sites on the differential binding ligand analogue complex to which the antibody can bind. So long as this minor adherence of the endogenous ligand binders to the differential binding ligand analogue complex does not affect the equilibrium existing between free ligand and that bound to the endogenous ligand binding receptors, then this effect will have little influence on assay results This is especially likely to be the case if the ligand analogue residue is a weak binder, but interference could well be expected if the ligand analogue residue in the differential binding ligand analogue complex binds strongly. In the case of thyroxine, the use of the strongly binding ligand thyroxine in the differential binding ligand analogue complex could promote interference by the endogenous protein binding receptors, whereas its homologue triiodothyronine, being a weak binder in comparison, would most likely not do so.

For an assay for the ligand free thyroxine, suitable materials to form an insoluble differential binding ligand analogue complex include polystyrene latex particles, (sometimes, but not essentially, containing ferromagnetic cores to enable separation of the differential binding ligand analogue complex by magnetic separation techniques) on to which the differential binding ligand analogue can be bound either covalently or by physical adsorption, or low density cellulose (sometimes, but not essentially, containing ferromagnetic cores to enable separation of the differential binding ligand analogue complex by magnetic separation techniques) which is covalently linked to L-triiodothyronine (or other ligand analogue) by activation of the cellulose using butane-1,4-diol diglycidyl ether. Differential binding ligand analogue coated polystyrene or cellulose particles not containing ferromagnetic cores can be separated in the assay system by centrifugation techniques. Alternatively, the triodothyronine or other suitable thyroxine-related ligand analogue with desired properties can be covalently joined to proteins through amide bonds, using standard chemical techniques, preferably, but not necessarily, through the triiodothyronine or ligand analogue amino group. The protein-ligand analogue may be insolubilised by absorption on to the internal walls of plastic tubes, or be cross-linked by an agent such as glutaraldehyde before such adsorption, in accordance with well-known techniques. Other methods, such as combined anti-(ligand antibody)-polyethylene glycol precipitations are also well-known methods of separating the reactants after incubation.

The anti-ligand antibody is purified from suitable hybridoma preparations by methods well known to those skilled in the art. The antibody can be raised specifically against the ligand it is desired to measure as free ligand in the final assay, or can be raised against suitable analogues of the ligand, with the proviso that the final antibody preparation consists of species avid for the ligand in any one case. Additionally, an antibody raised against the animal serum from which the monoclonal antibody was derived could be used as a second antibody for labelling (a universal antibody labelling reagent). The first (monoclonal) or second (universal) anti-antibody can be labelled by radioactive atoms such as 125-I, enzymes, chemiluminescent or fluorescent molecules.

The amount of anti-ligand antibody to be used should obey the limiting criteria set by valid free ligand assays (as described earlier) and should also be less than the amount of immobilised or insolubilised differential binding ligand analogue. Production of suitable dose-response curves, within these criteria, is done by experiment as routinely conducted in the art. Sera with defined free ligand concentrations can be used to establish a dose-response curve of acceptable sensitivity through the regions of clinical interest.

CHEMISTRY OF SYNTHESIS OF TRIIODOTHYRONINE-DERIVATISED CELLULOSE PARTICLES (THE DIFFERENTIAL BINDING LIGAND ANALOGUE COMPLEX)

The low density-cellulose particles with ferromagnetic cores (as described below) are reacted with butane-1,4-diol diglycidyl ether as shown:

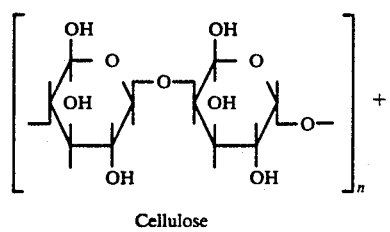

Cellulose

-continued

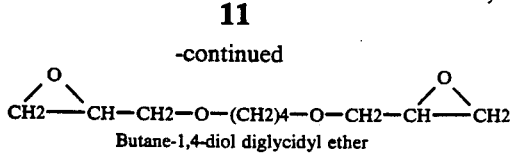
Butane-1,4-diol diglycidyl ether

The epoxide groups of the diglycidyl ether, situated at both ends of the molecule, will react readily with nucleophiles (e.g. —OH groups, —NH2 groups), in the following manner:

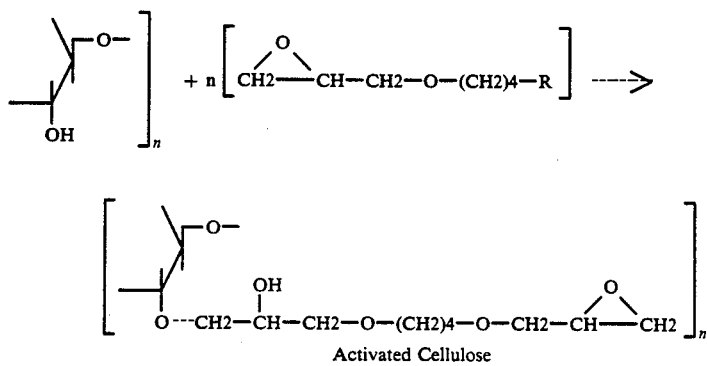
Activated Cellulose

Since any —OH groups of the cellulose may react, then many isomers of the activated complex are possible. Additionally, it is possible that for any attached —OH group of the cellulose, two stereoisomers of the added diglycidyl ether are possible:

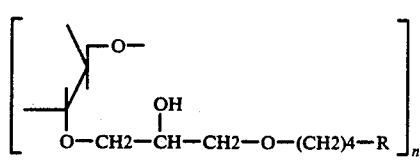
(A)

or

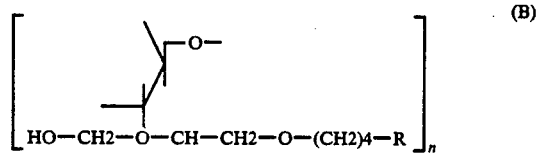
(B)

Alternative (A) is probably preferred sterically.

The activated cellulose is now reacted with triiodothyronine, to give two possible stereoisomers:

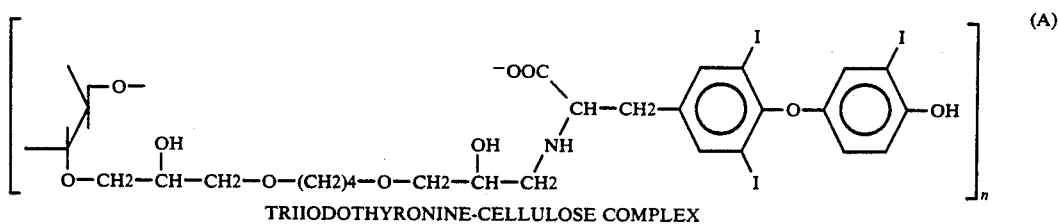
TRIIODOTHYRONINE-CELLULOSE COMPLEX or

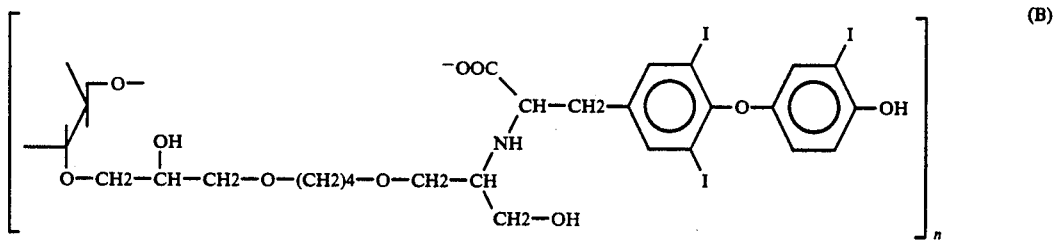
(B)

Again alternative isomer (A) is probably sterically preferred.

In the third stage, the remaining reactive groups in the derivatised cellulose are removed by reaction with ethanolamine:

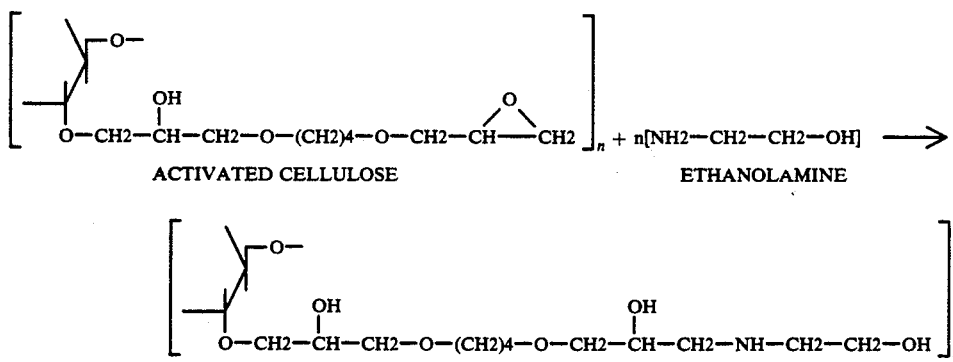

This is necessary to prevent crosslinking of cellulose particles by reaction of the remaining —OH group with other —OH groups on other cellulose molecules, which otherwise would promote aggregate formation.

PRODUCTION OF DIFFERENTIAL BINDING LIGAND ANALOGUE-COATED ACTIVATED CELLULOSE PARTICLES 20 milliliters (mls) of a suspension in water of low density cellulose particles (Scipac Ltd., Kent, U.K.) containing ferromagnetic cores, (particle content of ferric oxide nominally 25% w/w) (particle size range 2–10) and concentration 50 g/L was allowed to settle, then aspirated and centrifuged. The pellet of separated particles were resuspended in 20 mls water, allowed to settle and recentrifuged. This procedure was carried out three times. A further three cycles of washing the particles was carried out, resuspending each time in 20 mls 0.1M sodium hydroxide solution. The final suspension in 20 mls of the sodium hydroxide solution was then activated by adding 0.53 ml butane-1,4-diol diglycidyl ether and incubating the mixture for 100 minutes at 37° C. The suspension of activated cellulose particles was next taken through three cycles of centrifugation and resuspension into 20 mls 0.05M sodium carbonate/bicarbonate buffer, pH 9.6. Then, 13.3 miligrams of the sodium salt of L-triiodothyronine was added (using a solution in dimethylformamide). The mixture was incubated at 37° C. for 3 hours. The particle suspension was allowed to settle, aspirated and centrifuged and subjected to three cycles of washing in to 20 mls 0.05M sodium carbonate/bicarbonate buffer, pH 9.6. Next, 0.06 mls of ethanolamine was added to the 20 mls suspension of particles to block unreacted groups. Incubation of the mixture was carried out overnight at room temperature. The particle suspension was then taken through three cycles of centrifugation and resuspension in the carbonate/bicarbonate buffer, three in 0.1M sodium hydroxide solution, and three in 0.1M hydrochloric acid. The particles were finally suspended in 20 mls buffer containing 0.067M sodium and potassium phosphates, pH 6.7 (the diluent buffer). This was used routinely at a dilution of 1/100 in the assay.

SOURCE AND PROPERTIES OF THYROXINE-SPECIFIC MONOCLONAL ANTIBODY

A preparation of thyroxine-specific monoclonal antibodies derived from a mouse hybridoma was obtained from Immunosearch Inc, Toms River, New Jersey, USA. This clone (no. 02-911-112) was presented by the supplier as an immuno-globulin (subclass IgG2B) fraction in 0.015M potassium phosphate buffer (pH 7.2) containing 0.85% (w/v) sodium chloride and 0.1% (w/v) sodium azide. Purification of the immunoglobulin was achieved by column chromatography using diethyl-(aminoethyl)cellulose (DEAE), according to the suppliers protocols. The affinity constants of the antibody for thyroxine, triiodothyronine, and the triiodothyronine-complexed cellulose (see above) were measured by classical Scatchard analysis. The association constants at 37° C. were a) for thyroxine $4.6 \times 10^9$ L/mole, (quoted as approximately 0 L/mole by the supplier), b) for triiodothyronine $3.4 \times 10^7$ L/mole (suggesting approximately 1% cross-reactivity for antibody binding compared with thyroxine), and c) for the triiodothyronine-cellulose complex used as solid phase in the free tyroxine assay $6.7 \times 10^5$ L/mole. For comparison, a specimen of monoclonal anti-thyroxine antibody was taken through the standard iodination procedure for the production of iodinated-antibody, as described below, except that nonradioactive iodide was substituted for the radioactive material. On purification, this iodinated antibody gave the following association constants at 37°: a) for thyroxine, $4.4 \times 10^9$ L/mole, b) for triiodothyronine $4.0 \times 10^7$ L/mole and c) for the triiodothyronine-cellulose complex used as solid phase in the assay, $5.5 \times 10^5$ L/mole. For the iodinated and noniodinated antibody preparations, the affinities of the antibody were virtually identical for the same substances, and for thyroxine the antibody affinity was in each case much higher than for its cross-reacting analogue triiodothyronine. Complexing of triiodothyronine to the cellulose particles reduced the affinity of the antibody for the complex still further, presumably due largely to additional steric hindrance and "bulky molecule" effects as described earlier. A further contribution to the apparently grossly lowered affinity of the antibody for the triiodothyronine-cellulose complex could be due additionally to the unavailability of a portion of the complexed triiodothyronine residues for binding by the antibody. However, the affinity of the antibody for thyroxine was considerably smaller than specified in W 83/03306 as being essential for a viable free thyroxine assay. The monoclonal antibody preparation was stored in the buffer as received from the supplier (see above) until required, at a concentration of 1 g/L.

PREPARATION OF 125-I LABELLED ANTI-THYROXINE ANTIBODIES

In the reactions described below, all manipulations were carried out at room temperature (c. 20° C.). The following reagents were first mixed together: 45mCi (1.67 GBq) [125-I]-sodium iodide (Amersham International, code IMS 300, concentration range 350–600 mCi/ml (12.9–22.2 GBq/ml)) in 0.1M sodium phosphate buffer pH 6.0 containing 0.3M NaCl; 0.6 ml of a solution of the monoclonal anti-thyroxine antibody preparation, concentrated to 5 mg/ml by freeze-drying and resuspension in 0.1 ml 0.1M sodium phosphate buffer, pH 7.5. Then, 0.02 ml of a chloramine-T solution (containing 10 mg/ml chloramine-T in the same phosphate buffer) was added, and the solution was mixed for 5 seconds. The mixture was incubated for 55 seconds, when 0.02 ml sodium metabisulphite solution (20 mg/ml sodium metabisulphite in the same phosphate buffer) was added to stop the reaction. The mixture was applied to a high performance liquid chromatography column of Superose 12 [HR 10/30], dimensions 1 cm×30 cm, (Pharmacia Ltd.) and eluted with a buffer of 0.1M sodium phosphate 0.3M sodium chloride, pH 6.0 at an elution rate of 1 ml/min. The emerging labelled antibody peak was detected by an ultraviolet absorbance detector at 280 nm, and the matching radioactivity profile of the labelled antibody was followed. The [125-I]-labelled anti-thyroxine antibody preparation was collected in 2–3 ml fluid, eluting from the column after about 20 minutes. The specific activity of the labelled antibody reparation was $2.4\times 10^6$ mCi/mmole (88.8 TBq/mmole) protein. This indicated approximately one radioatom of 125-I per molecule of antibody. The amount of [125-I]radioactivity per assay tube was thus about 0.05 microcuries (18.5 hBq) [$1.1\times 10^5$ dpm].

DESCRIPTION OF THE IMMUNOMETRIC ASSAY FOR SERUM/PLASMA FREE THYROXINE 50 microliters of a serum sample was mixed with 0.5 ml of the solid-phase triiodothyronine (T3)-conjugated cellulose complex suspension (concentration 0.5 g/L, see paragraph on preparation for the working strength concentration) containing 253 pmol complexed T3. 0.5ml [125-I]-labelled anti-thyroxine antibody solution (containing 3 ng [20 fmol] antibody) was then added. The molar ratio of complexed T3 to [125-I]-labelled antibody was approximately 12600/1. The solution was vortex mixed, and was incubated at 37° C. for 30 minutes. Free thyroxine in the serum competed with the T3-cellulose complex for binding the [125-I]-labelled anti-thyroxine antibody, and the fraction of [125-I] counts bound to the complex was inversely proportional to the serum free thyroxine concentration. The magnetised T3-cellulose complex with associated [125-I]-antithyroxine antibody was now precipitated by placing the tubes containing the reaction mixture on to a rack with a magnetised base (Amersham International Plc) so that the insoluble T3-cellulose complex was attracted to the bottom of the tubes, forming a stable pellet. A period of 10 minutes in contact with the magnetised separation rack sufficed to complete the separation of the cellulose complex from solution. The tubes were next inverted (in contact with the rack) to discard the solution, and after draining in the inverted position for 5 minutes, the tubes containing only the labelled antibody attached to the magnetised T3-cellulose particles were then counted for 60 seconds in the usual way, using a standard radioisotpe detector for [125-I]emissions. The free thyroxine concentrations of unknown sera were interpolated from a dose-response curve, constructed using samples with known free thyroxine concentrations and spanning the whole assay range of expected values. A typical dose-response curve is shown in FIG. 1.

Assays using other preparations of anti-thyroxine monoclonal antibodies, with association constants for thyroxine of about $10^8$ L/mole, were impractical, owing to a low B(o) of <5%, using T3-cellulose, indicating that less avid antibodies were unsuitable for the development of assays according to this invention. However, T4-cellulose gave a usable curve, because the affinity constant of the antibody is closer to $10^8$ L/mole (i.e. within permissible value ranges). A reasonable estimate of the range of antibody association constants for binding with the ligand analogue-cellulose solid phase complex, giving usable dose-response relationships for free thyroxine estimation, is thus $10^5$ to $10^8$ L/mole This covers lower limits, below which stable binding of the antibody to the ligand analogue-cellulose solid phase may be unattainable, and upper limits, above which the association constant of an antibody for the complex approaches that for thyroxine, thus limiting the desirable amount of ligand analogue-cellulose complex (see earlier argument).

The product of the association constant (Kab) of the antibody and the concentration (C) of the T3-cellulose solid phase complex was $5.5\times 10^5 \times 2.53 \times 10^{-10}$ or $1.39\times 10^{-4}$. Similarly for the free thyroxine, the corresponding product was $4.6\times 10^9 \times 1.5 \times 10^{14}$ or $6.9\times 10^{-5}$ (if it is assumed that about 0.3% of the available hormone in 0.05 ml of a euthyroid serum containing $10^{-7}$ mole/L thyroxine is sequestered by the antibody). The close similarity of the Kab x C product values for the competing T3-cellulose complex and sequestered thyroxine is a demonstration of the approximate equivalence of the effective avidity of the antibody for either moiety and predicts a workable dose-response curve.

Figure 2:
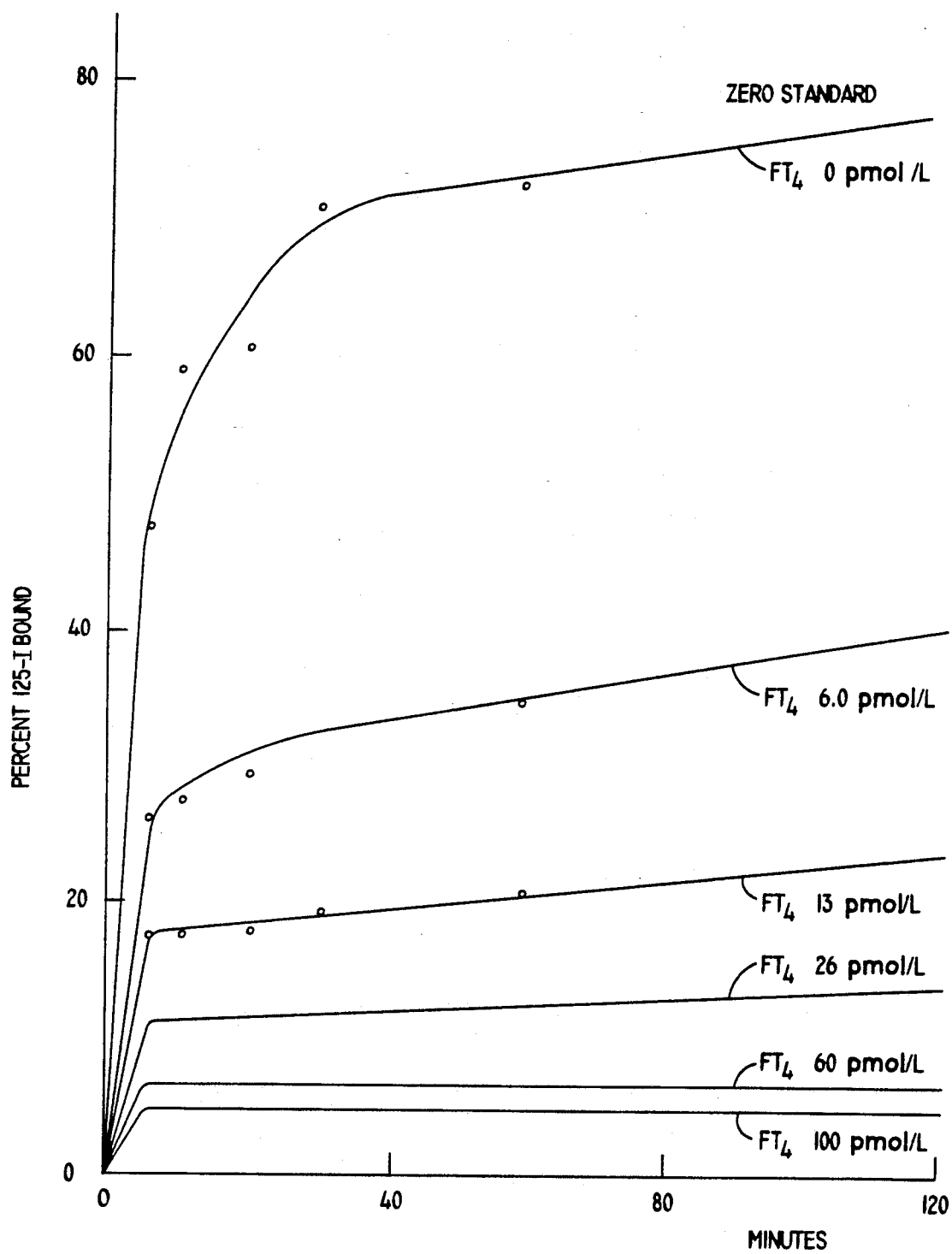
FIG. 2 shows the kinetics of approach to equilibrium of a labelled antibody bound to a T3-cellulose solid phase, using sera with various known free thyroxine concentrations.

FIG. 2 shows the kinetics of approach to equilibrium of the labelled antibody bound to the T3-cellulose solid phase, using sera with various known free thyroxine concentrations. The assay had virtually achieved full equilibrium by 30 minutes at 37° C.

The affinity constant of the iodine-labelled antibody for thyroxine in the assay was $<5\times 10^9$ L/mole According to the teaching of Patent Application WO 83/03306, and additional writings by its author in reference to the matters discussed in the invention covered by this Application, the use of antithyroxine antibodies with affinity constants well below the value given by the reciprocal of the serum free thyroxine concentration (typically about $1.3\times 10^{-11}$ mol/L) should give extremely insensitive and unusable dose-response curves.

Inspection of the equation describing the binding of thyroxine to the antibody in a free thyroxine assay (see earlier) reinforces this expectation, if it is assumed that the assay proceeds purely by classical Mass Action equilibrium principles. In the denominator of the equation [FT4].Kab.Pab/(1+Kab[FT4]) as given earlier to describe the binding of free thyroxine to the antibody, a value for Kab much less than $10^{11}$ L/mole makes the magnitude of Kab[FT4] much less than unity for all physiologically real values of [FT4], and thus indicates that usable dose-responses should not be obtained if Kab $<<5\times 10^{10}$ L/mole.

The working of the invention more plausibly emerges from considering that, throughout the reaction of the labelled antibody with the competing solid phase T3-cellulose complex and the serum free thyroxine (continually released from the serum thyroxine-binding proteins as it is taken up by the antibody), the effective concentrations of both competing moieties do not essentially alter over the course of the binding reaction with the labelled antibody. Owing to the negligibly small fraction of thyroxine taken up by the labelled antibody, the free thyroxine concentration is virtually unaltered by readjustment of the serum free-bound equilibria, and the very large molar excess of the weak binding T3-cellulose complex over the concentration of labelled antibody ensures that the concentration of available binding sites for antibody remains virtually the same over the course of the reaction. There is thus a simple competition between a constant concentration of free thyroxine and free T3-cellulose binding sites for binding the antibody, based only on their relative affinities and concentrations. Thus, the forward rates of association of the labelled antibody to either free thyroxine or unbound sites on the T3-cellulose binding complex are of the form $K(a)[fAn][fPab]$, where $K(a)$ is either the association constant of the antibody for the analyte or the differential binding ligand analogue, and $[fAn]$ is the concentration of either free analyte or available sites on the differential binding ligand analogue. $[fPab]$ represents the concentration of unoccupied sites on the antibody.

An additional finding arguing against a classical Mass Action explanation for the assay s mode of operation comes from the finding of negligible rates of "back-replacement" of preformed T3-cellulose-[125-I]-antibody complex by free thyroxine. A standard assay of a group of sera containing various concentrations of free thyroxine was first carried out, and the [125-I]-labelled antibody bound to the T3-cellulose particles was separated by magnetic separation as described earlier. The particles were then resuspended in 1 ml tracer buffer, though no further antibody was added, and incubated with a further aliquot of serum for up to 240 minutes in the usual assay conditions. The T3-cellulose-[125-I]-antibody complex was then repelleted using the magnetic separator.

TABLE 1 indicates that there was only a very slow rate of "back reaction" of antibody, bound to the T3-cellulose in the first incubation, to form significant amounts of antibody bound to soluble free thyroxine in the second incubation, over a period up to 8 times longer than the recommended assay incubation time. If the first incubation had proceeded by an approach to an equilibrium between equally rapid forward and back reactions then significant and rapid displacement of antibody from the T3-cellulose would have been expected in the second incubation. This suggests that the assay is described better in "quasi-" rather than "true" equilibrium terms.

The experimental findings thus indicate that the assay proceeds by a simple, rapid forward competitive reaction between essentially unchanged concentrations of the reactant free thyroxine and binding sites on a magnetised T3-cellulose solid phase complex until saturation of the [125-I]-antibody binding sites is effectively achieved. The rate of dissociation of thyroxine or T3-cellulose from the antibody is so slow that this factor is a negligible contributor to the kinetics of reaction over the duration of the assay incubation period of 30 minutes.

TABLE 1

ABSENCE OF RAPID "BACK REACTION" IN THE "EQUILIBRATED" FREE THYROXINE ASSAY

| Serum Sample | % [125-I]-antibody bound to the magnetised T3-cellulose solid phase Serum After Indicated Time (Min) of 2nd FT4 Incubation With New Serum Sample (pmol/L) | | |
|---|---|---|---|
| | 15 | 90 | 240 |
| Controls (Amerlex-M FT4 RIA Kit) | | | |
| H (Hypo) | 4.7 | 33.0 | 31.5 | 29.8 |
| I (Euth) | 11.3 | 18.2 | 15.9 | 15.2 |
| K (Hyper | 78.8 | 4.0 | 3.4 | 2.5 |
| P-21 (Preg) | 8.7 | 22.6 | 19.3 | 18.9 |
| RIA 3 | 41.8 | 6.3 | 5.1 | 4.7 |
| Patient Samples (Euthyroid) | | | |
| 1 | 10.2 | 19.5 | 17.2 | 16.6 |
| 2 | 11.0 | 18.4 | 16.5 | 15.1 |
| 3 | 17.1 | 13.3 | 11.2 | 10.5 |
| 4 | 16.3 | 13.7 | 11.5 | 11.0 |
| 5 (Zero TBG) | 14.0 | 14.9 | 13.8 | 12.4 |

Experiments using a thyroxine-cellulose complex instead of the T3-Cellulose complex described in this invention gave similar results, with similar slow reductions in the precentage of [125-I]-labelled antibody bound to the solid phase during prolonged incubation.

PERCENTAGE OF SERUM THYROXINE SEQUESTERED IN ASSAY

A valid free thyroxine assay must obey the central criterion of sequestering so small a percentage of the available thyroxine in serum (bound . free) that the automatic readjustment of the equilibria governing the bound-free relationship in serum does not significant alter the free thyroxine concentration. This sequestration should not be greater than about 5% of the total thyroxine in a given serum. Accordingly, five sera were examined for their ability to test this criterion to its fullest extent; a) a hypothyroid-, b) a normal-TBG euthyroid-, c) a hyperthyroid-, d) a 3rd trimester pregnant (high TBG)- and e) a euthyroid zero-TBG serum.

In the experiment, 0.5 ml of serum was equilibrated with 10 microliters of [125-1]-labelled thyroxine (high specific activity, Amersham International Plc, code IM 141) for 30 minutes. To 50 microliter aliquots was added 0.5 ml of the T3-cellulose solid phase suspension at the concentration used in the assay procedure. To one aliquot of the mixture, 0.5 ml of the buffer used in the [125-I]-labelled antibody solution in the assay method was added (to act as a correcting "blank"). To another aliquot was added unlabelled anti-thyroxine antibody in this buffer, with an antibody concentration 25 times that used in the assay procedure. All tubes were now incubated, after mixing, for 30 minutes at 37° C. Then 1.5 ml of 50% (w/v) polyethylene glycol (PEG 6000) solution was added, the tube contents were vortex mixed and centrifuged at 1500×g for 20 minutes. The antibody immunoglobulins were precipitated by the polyethylene glycol, taking with them whatever [125-I]-thyroxine was bound to the antibody binding sites After decanting away the supernatant fluids, the pellets were resuspended in 0.5 ml water and were again precipitated and centrifuged using polyethylene glycol. After decantation, the pellets were counted for 1 min. After correcting for "blank" effects, the percentage of [125-I]-thyroxine bound to the antibody was calculated and corrected for the 25-fold greater antibody concentration than usually present in the standard assay. The results are shown in TABLE 2.

TABLE 2
PERCENTAGE OF SERUM THYROXINE BOUND BY THE ANTIBODY IN THE FREE THYROXINE ASSAY

| SERUM TYPE | PERCENTAGE [125-I] THYROXINE BOUND TO ANTIBODY |
| --- | --- |
| Hypothyroid | 0.21 |
| Euthyroid-normal TBG | 0.20 |
| Hyperthyroid | 0.19 |
| 3rd trimester pregnant | 0.08 |
| Euthyroid-zero TBG | 0.75 |

In all cases, the percentage of total serum thyroxine sequestrated by the antibody in the assay conditions was well within the criterion established as necessary for a valid free thyroxine assay.

DILUTION CHARACTERISTICS OF THE FREE THYROXINE ASSAY

It has been shown that, even in the most searching case of a zero-TBG subject, where the lack of TBG in serum leads to a relatively low total thyroxine concentration enabling a normal free thyroxine level (and thus the potential of too great a sequestration of thyroxine by the antibody in the assay for validity), the percentage of thyroxine uptake by the [125-I]-labelled antibody is still within the criterion limits defined. Thus, provided that the [125-I]-labelled antibody and/or the solid phase T3-cellulose binding complex do not interact significantly with any of the endogenous thyroxine-binding proteins (TBG, TBPA or albumin), progressive dilution of serum should not lead to significant changes in the measured free thyroxine concentration until samplings of approximately 5% total thyroxine are made. This is because, up to this point, the bound-free thyroxine equilibrium in serum can tolerate such levels of sequestration and can quickly readjust to maintain virtually constant free thyroxine concentrations. This should be less true of hyperthyroid sera, because there is a greater tendency for the loss of bound thyroxine to the free phase to alter the ratio of bound/free sites found on the endogenous serum binding proteins (especially TBG) and thus free thyroxine levels. To test the performance of the free thyroxine assay described above for its responses to further dilution of serum, several hypothyroid, euthyroid, hyperthyroid and 3rd trimester pregnancy samples were used. The samples were measured for free thyroxine concentrations either undiluted or diluted ½ or ¼ using 0.01M HEPES buffer pH 7.4. The results are shown in TABLE 3.

TABLE 3
ROBUSTNESS OF IMMUNOMETRIC FREE THYROXINE ASSAY TO DILUTION OF SERUM SAMPLES (ADDITIONAL TO THE ASSAY DILUTION FACTOR OF 1/21)

| SERUM TYPE | ADDITIONAL DILUTION FACTOR FOR SERUM | | |
| --- | --- | --- | --- |
| | UNDILUTED | ½ | ¼ |
| Hypothyroid 1 | 10.2 | 13.6 | 9.9 |
| Hypothyroid 2 | 8.9 | 8.6 | 8.7 |
| Euthyroid 1 | 10.0 | 13.0 | 10.0 |
| Euthyroid 2 | 15.6 | 15.3 | 13.6 |
| Euthyroid 3 | 19.0 | 20.0 | 15.7 |
| Euthyroid 4 | 22.0 | 22.0 | 16.3 |
| Pregnant 1 | 13.3 | 14.3 | 14.3 |
| Pregnant 2 | 12.8 | 11.4 | 11.2 |
| Zero TBG Euthyroid | 17.7 | — | 10.6 (1/5 dilution) |
| Hyperthyroid 1 | 71.7 | 46.0 | 28.5 |
| Hyperthyroid 2 | 75.7 | 55.8 | 35.4 |
| Free Thyroxine Concentration (pmol/L) | | | |

As expected the hypothyroid, euthyroid and pregnancy sera showed good responses to serum dilution, and gave nearly constant values over dilution, for the reasons given above. Similarly, the zero-TBG euthyroid specimen was affected by dilution, owing to the fact that the percentage of thyroxine sequestereated by the antibody in undiluted serum was already considerably higher than for other sera, thus reducing the range over which robustness to dilution is expected. The assay thus demonstrates good performance in a classical test of free thyroxine assay validity as, in euthyroid or hypothyroid sera, a dilution factor of four reduced measured free thyroxine values by only about 10–20%.

NONINTERFERENCE OF ENDOGENOUS SERUM THYROXINE-BINDING PROTEINS IN THE FREE THYROXINE ASSAY

The serum thyroxine-binding proteins presenting most difficulty, as regards their potentials for interference in a free thyroxine assay, are TBG and albumin. The former must be excluded as a potential interferent because it is the principal thyroxine binding protein in serum, and minor binding of TBG to the T3-cellulose solid phase might cause distortion of free thyroxine estimations (through competition of TBG with the [125-I]-labelled anti-thyroxine antibody for binding) and thus produce a correlation of the assay with serum TBG concentration. Similarly, the possibility that albumin may interfere with antibody binding to the solid phase must also be examined, as in assays for free thyroxine using labelled analogues of thyroxine it has been found difficult to prevent the residual binding of such analogues to albumin. Indeed, addition of reagents capable of "blocking" the binding sites of serum albumin that are otherwise able to sequester a portion of the labelled analogue of the ligand thyroxine has been described for improved "analogue" free thyroxine radiommunoassays (European Patent Application 0 155 104), aimed at reducing this unwanted correlation of results with the concentration of albumin in serum.

The possibility that these phenomena might affect the present invention was checked as follows. Pure TBG containing no detectable thyroxine was added to the "zero" standard of the Amerlex-M free thyroxine radioimmunoassay (marketed by Amersham International Plc as the Amerlex-M FT4 RIA kit, code IM3050) at various concentrations. The "zero" standard of the kit consisted of an otherwise normal serum (with respect to TBG, TBPA and albumin concentrations) but containing no thyroxine (removed by ion-exchange stripping). Thus, for all concentrations of TBG listed in Table 4, a further 20 mg/L should be added to include the endogenous TBG content of the standard. Similarly, pure human serum albumin, free from bound thyroxine, was added to other aliquots of the "zero" standard. A concentration of 40 g/L should be added to the concentrations listed in Table 4 to account for the endogenous albumin present in the standard Experiments were carried out using the concentrations of T3-cellulose solid phase, [125-I]-labelled antibody, serum volume and incubation conditions as used in a normal assay. The Table shows no effect of adding up to 150 mg/L exogenous TBG or 100 g/L human serum albumin on the B(o) value of the assay as shown by the "zero" standard As the highest concentrations of either TBG or albumin added are considerably greater than the largest concentrations encountered physiologically in serum, this shows that the assay is not subject to detectable interference from these proteins.

TABLE 4

EFFECT OF ADDED TBG OR HUMAN SERUM ALBUMIN ON THE B(o) VALUE OF THE FREE THYROXINE ASSAY

| CONCENTRATION OF TBG ADDED (MG/L) | CONCENTRATION OF ALBUMIN ADDED (G/L) | B(o) VALUE FOR ZERO STANDARD (%) |
|---|---|---|
| 0 | — | 69.1 |
| 37.5 | — | 70.2 |
| 75 | — | 69.6 |
| 150 | — | 67.1 |
| — | 0 | 69.7 |
| — | 25 | 68.9 |
| — | 50 | 68.7 |
| — | 100 | 68.6 |
| (+20 mg/L endogenous) | (+40 g/L endogenous) | |

Additionally, the constancy of the assay free thyroxine estimations in serum diluted by factors of up to four in buffer both indirectly confirms the above findings, and also indicates that TBPA does not interfere in the assay to any significant extent, as otherwise the dilution characteristics of the assay would be compromised as the TBPA concentrations fell on progressive serum dilution.

PERFORMANCE OF THE FREE THYROXINE ASSAY IN PANELS OF PATIENT'S SERA

Figure 3:
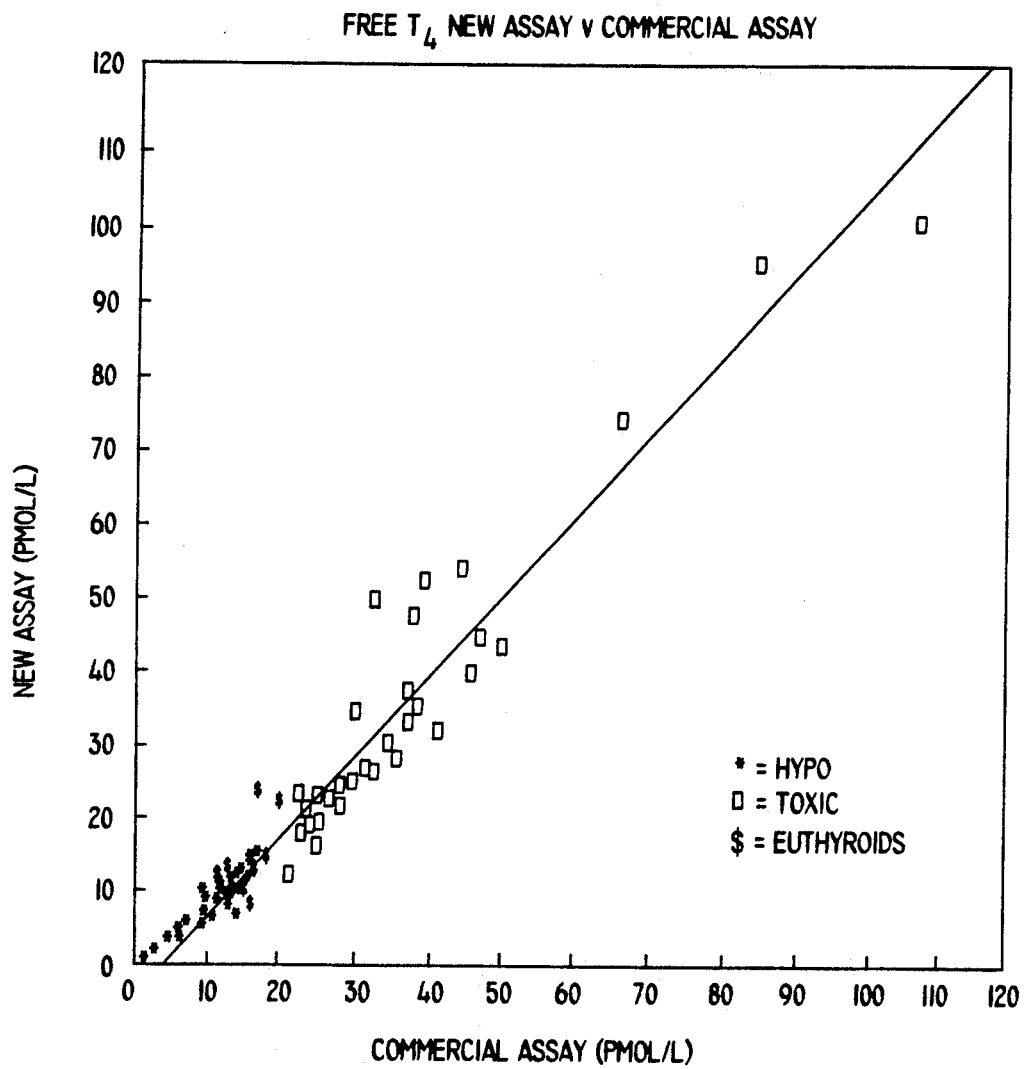
FIG. 3 illustrates graphically the correlation between the assay method of this invention applied to free thyroxine, and a commercially available free T4 assay.

A panel of euthyroid (n=37), hypothyroid (n=34) and hyperthyroid (some on antithyroid treatment) (n=40) sera were assayed for free thyroxine by the technique described in this invention, compared against values obtained by a method already commercially available as an "analogue" free thyroxine assay method (Amerlex-M FT4 RIA kit, Amersham International Plc). the results are shown in FIG. 3.

There was a good and highly significant (p<0.001) correlation between both assays ( r=0.965), with similar good discrimination of the various patient groups. The slope of the correlation line was 1.052. This demonstrates equivalence of the new assay with existing accepted methods for measuring serum free thyroxine concentrations. The ranges for free thyroxine for the hypothyroid, euthyroid and 27 hyperthyroid sera (those with values above the normal range in the comparative "analogue" assay) are shown in Table 5.

TABLE 5

| SERUM GROUP | N | IMMUNOMETRIC FT4 (PMOL/L) | ANALOGUE FT4 (PMOL/L) |
|---|---|---|---|
| Hypothyroid | 34 | 0.7–13.4 | 1.1–14.8 |
| Euthyroid | 37 | 8.3–27.3 | 9.6–23.8 |
| Hyperthyroid | 27 | 23.1–109.3 | 26.5–108 |
| Normal Range | | 8.8–26 | 9–25* |

*as given in the product literature for the analogue free thyroxine assay.

The assay also showed no significant correlation of results with the serum concentrations of albumin or TBG, as forecast from the lack of effect on the binding of [125-I]-labelled antibody to the T3-cellulose solid phase (shown in Table 4). Table 6 shows results for sera from euthyroid subjects with low (absent) or high concentrations of TBG, and with either low concentrations of serum albumin (analbuminemia) or possessing a high serum concentration of the molecular form of albumin containing an unusually strong binding site for thyroxine (the syndrome of familial dysalbuminemic hyperthyroxinemia [FDH}). In contrast to the "analogue" free thyroxine assay (where it is known that there is residual binding of the labelled analogue tracer to either normal albumin or the form found in the FDH syndrome, thus distorting the results in this assay method in either FDH or analbuminemia), the immunometric assay in this invention is unaffected and gives normal results. Serum containing avid autoantibodies to thyroid hormones (which affect the analogue assay because of tracer sequestration by the endogenous antibody molecules) are also measured appropriately in the immunometric assay. Also shown are results from subjects suffering from a variety of nonthyroidal illnesses, but who were otherwise judged to be euthyroid. The results again support the concept that the assay corrects for variation in serum TBG concentration, as should occur in a valid free thyroxine assay, and is also unaffected by variation in albumin concentration or binding affinity.

TABLE 6

PERFORMANCE OF THE IMMUNOMETRIC ASSAY ON PATIENT SAMPLES WITH ABNORMAL CONCENTRATIONS OR AFFINITIES OF ENDOGENOUS THYROXINE-BINDING PROTEINS

| | | FREE THYROXINE ESTIMATION (PMOL/L) | |
|---|---|---|---|
| SERUM TYPE | N | IMMUNO-METRIC ASSAY | ANALOGUE ASSAY (COMMERCIALLY AVAILABLE) |
| NORMAL EUTHYROID (to give normal range estimate) | 37 | 9–26 | 10–24 |
| LOW (ZERO) TBG | 2 | 16.4, 15.5 | 16, 18 |
| HIGH TBG (Non-pregnant) | 9 | 17.1 +/− 7.9 | 16.3 +/− 6.4 |
| 3rd TRIMESTER PREGNANT | 25 | 11.8 +/− 2.7 | 10.1 +/− 2.7 |
| FDH SYNDROME | 13 | 11.4 +/− 2.3 | not done but generally above normal range |
| NONTHYROIDAL ILLNESS | 76 | 14.6 +/− 4.5 | 14.6 +/− 4.1 |
| ANALBUMINEMIA | 1 | 20.0 | 10.0 |
| THYROID HORMONE | 2 | 8.7, 19.2 | 48.6, 137 |

TABLE 6-continued

PERFORMANCE OF THE IMMUNOMETRIC ASSAY ON PATIENT SAMPLES WITH ABNORMAL CONCENTRATIONS OR AFFINITIES OF ENDOGENOUS THYROXINE-BINDING PROTEINS

| SERUM TYPE | N | FREE THYROXINE ESTIMATION (PMOL/L) | |
|---|---|---|---|
| | | IMMUNO-METRIC ASSAY | ANALOGUE ASSAY (COMMERCIALLY AVAILABLE) |
| AUTOANTIBODIES | | | |

The results show equivalence with the commercially available "analogue" radioimmunoassay for free thyroxine in conditions of TBG variance (low and high TBG nonpregnant, third trimester pregnant) and nonthyroidal illness (normal TBG but modest reductions in albumin concentration). However, the immunometric assay shows better performance in those cases of extreme variation in albumin concentration or affinity for thyroxin binding (FDH syndrome, analbuminemia) and where thyroid hormone-binding autoantibodies exist in serum. This agrees with the knowledge that the "analogue" assay has a small dependence on albumin concentration or affinity in serum, affecting the results when the albumin is very different from the norm. The immunometric assay, being unaffected by albumin, does not show this dependence.

EXAMPLE 2

Immunometric Assay for Free Testosterone

Production of Differential Binding Ligand Analogue-Coated Activated Cellulose Particles Twenty ml of a suspension in water of activated low density cellulose particles was prepared as described in Example 1. Etiocholan-17β-ol-3-carboxmethyloxime (5β-DHT-3CMO) was prepared by standard methods, by reacting 5-DHT with carboxymethyloxime hemihydro-chloride. The product was purified by extraction and recrystallisation. The 5β-DHT-3CMO was coupled to bovine serum albumin (BSA) using the active ester method, and purified by gel filtration chromatography before freeze drying. The DHT-incorporation was determined by measuring the number of amino groups coupled, using trinitro benzene sulphonic acid. This preparation gave a DHT:BSA ratio 5:1. A solution of 5β-DHT-3CMO-BSA in the carbonate/bicarbonate buffer was prepared at a dilution of 125 mg/ml.

0.5 ml of this solution was then added to the activated cellulose. The mixture was incubated at 37° C. for two hours. The particle suspension was allowed to settle, aspirated and centrifuged and subjected to three cycles of washing in 10 ml lots of 0.05M carbonate/bicarbonate buffer pH9.6, followed by three wash cycles of 0.1M NaOH and three cycles of 0.1M HCl. Finally the particles were washed three times in 0.1m phosphate buffer pH7.0 and were re-suspended in 20 ml of the phosphate buffer. For the assay, the particles were diluted 1/10 in the same buffer.

Source and Properties of Testosterone-Specific Monoclonal Antibody

A preparation of testosterone specific monoclonal antibody was obtained from Interpharm Laboratories, Israel. The antibodies were produced from a clone made by hybridisation of N50/1 mouse myeloma cells and spleen cells of Wistar rats immunised with BSA conjugated testosterone-3-carboxymethyl oxime. This clone (number F2) was presented by the supplier as a highly purified immunoglobulin (subclass IgG1) lyophilised fraction. The affinity constant of the antibody was quoted by the suppliers to be $1 \times 10^{10}$ l/mole. Its cross-reactivity to 5β-DHT was quoted as 15%. The affinity constant of the antibody for the insolubilised 5β-DHT was estimated as $1.5 \times 10^{7}$ l/mole Preparation of 125-I Labelled Anti-Testosterone Antibodies In the reactions described below, all manipulations were carried out at room temperature (about 20° C.). The following reagents were first mixed together: 1.0 mCi of 125-I sodium iodide in 0.1M potassium phosphate buffer pH6.0 containing 0.3M NaCl; 0.05ml of a solution of the monoclonal anti-testosterone antibody preparation, at concentration of 2mg/ml in distilled water. Then 0.04 ml of a chloramine-T solution (containing 100 µg/ml chloramine-T in potassium phosphate buffer pH7.5) was added, and the solution was mixed for five seconds The mixture was incubated for sixty seconds, when 0.04 ml sodium metabisulphite solution (200 µg/ml sodium metabisulphite in the same phosphate buffer) was added to stop the reaction. The mixture was applied to size-exclusion chromatography using Sephadex S25 (PD-10 column, Pharmacia Ltd.) and eluted with 0.1M potassium buffer plus 0.1% BSA, pH7.5. The emerging labelled antibody peak was eluted in the void volume of the column The specific activity of the labelled antibody preparation was $1.5 \times 10^{6}$ mCi/mmole protein.

Description of the Immunometric Assay for Serum/Plasma Free Testosterone

50 µl of a serum sample was mixed with 0.2 ml of the solid phase 5β-DHT-3CMO-BSA-conjugated cellulose complex suspension. 0.2ml of the labelled anti-testosterone antibody (containing 5ng, 33fmol, antibody) in 0.1M potassium phosphate plus 1% BSA buffer pH7.5, was then added. The solution was vortex mixed, and was incubated at 37° C. for 1 hour. Free testosterone in the serum competed with the 5β-DHT-cellulose complex for binding the labelled antibody, and the fraction of 125-I bound to the complex was inversely proportional to the serum free testosterone concentration. The magnetised 5β-DHT-cellulose complex with associated antibody was now precipitated by placing the tubes containing the reaction mixture on a rack with a magnetised base so that the insoluble 5β-DHT-cellulose complex was attracted to the bottom of the tubes, forming a stable pellet. A period of 10 mins. in contact with the magnetised separation rack sufficed to complete the separation of the cellulose complex from solution. The tubes were next inverted (in contact with the rack) to discard the solution. The pellets were then resuspended in 1ml water, placed again on the magnetic rack for 10 mins and then inverted. After draining in the inverted position for 5 mins, the tubes containing only the labelled antibody attached to the magnetised 5β-DHT-cellulose particles were then counted for sixty seconds. The free testosterone concentrations of unknown sera were interpolated from a dose-response curve, constructed using samples with known free testosterone concentrations and spanning the whole assay range of expected values. The following results are typical of those obtained.

| Free Testosterone (pg/ml) | Radioactive cpm in precipitate | % Radioactivity bound |
| --- | --- | --- |
| 0 | 34,726 | 23.2% |
| 1 | 28,843 | 19.2% |
| 4.2 | 23,313 | 15.5% |
| 12.5 | 18,144 | 12.1% |
| 35 | 13,435 | 9.0% |
| 100 | 8,885 | 5.9% |
| 250 | 6,264 | 4.2% |

The affinity constant of the antibody for the analogue was $1.5 \times 10^7$ l/mole; the effective concentration of the analogue was $1.7 \times 10^{-8}$ moles per assay tube; the product of these two figures is $2.6 \times 10^{-1}$. The affinity constant of the antibody for the ligand was $1 \times 10^{10}$ l/mole; the concentration of ligand bound to antibody at the end of the incubation was estimated at $4 \times 10^{-11}$ moles; the product of these two figures is $4 \times 10^{-1}$. The ratio of these two products is 0.65. The ratio of the effective analogue concentration to the antibody concentration is about $5 \times 10^4$.

Non-Interference of Endogenous Sex Hormone Binding Globulin in the Free Testosterone Assay Testosterone is transported in the blood stream of human beings largely bound to two naturally occuring proteins SHBG (TsBG) and albumin. In women some 79% of testosterone is bound to SHBG (TsBG). Levels of SHBG (TsBG) and consequently total testosterone concentrations increase during pregnancy. However, free testosterone concentrations in pregnant women are not significantly different from those in non-pregnant women.

A panel of non-pregnant women (n=38) and third trimester pregnant sera (n=25) were assayed for free testosterone by the technique described above. The mean (±SD) free testosterone concentration in the non-pregnant sera was 15.6±5.06 pg/ml, which was not significantly different from that of the pregnant panel (12.5±2.9 pg/ml).

EXAMPLE 3

Immunoradiometric Assay for Free Tri-Iodothyronine (T3)

Reagents

Anti-T3 monoclonal antibody was raised in-house using T3-BSA complex purified by standard techniques, and was then labelled with 125-I as described in Example 1.

The ligand analogue was di-iodothyronine (T2). This was linked to activated cellulose by the technique described in Example 1.

The affinity constant of the labelled antibody for T3 was $5 \times 10^9$ l/mole; the affinity constant of the labelled antibody for T2 was $1 \times 10^8$ l/mole; the affinity constant of the labelled antibody for the insolubilised T2 was estimated as $5 \times 10^6$ l/mole.

Assay Method

50 μl of a serum sample was mixed with 0.5ml of a suspension of the T2-cellulose particles containing $2.5 \times 10^{-9}$ moles/l T2 ($0.25 \times 10^{-10}$ moles of T2 on $1.25 \times 10^{-4}$g of cellulose per assay tube); and 0.5 ml of a solution of the labelled antibody containing $5 \times 10^{-15}$ mole of labelled antibody per tube. Dilution buffers, incubation conditions and magnetic particle separation were as described in Example 1. The following results are typical of those obtained.

| Free T3 (pg/ml) | % Radioactivity bound |
| --- | --- |
| 0 | 39 |
| 2.5 | 37 |
| 5 | 32 |
| 10 | 30 |
| 20 | 22 |
| 40 | 16 |

In this assay, product a) (the affinity constant of the labelled antibody for the analogue times the effective concentration of the analogue) is $1.25 \times 10^{-2}$; and product b) (the affinity constant of the antibody for the ligand times the concentration of ligand bound to antibody at the end of the incubation) is $3 \times 10^{-2}$. The ratio of a) to b) is thus 0.4. The ratio of the effective analogue concentration to the antibody concentration is about $5 \times 10^4$.

EXAMPLE 4

Components

T3-Gelatin 1.5 mg T3 dissolved in 1.5 ml 0.1M NaOH Gelatin (Type Sigma G9382) was made up to 5 mg/ml in warm distilled water.

To 1.5mg T3 (in 1.5 ml) was added 1 ml gelatin solution and mixed. 40 μl grade I glutaraldehyde (Sigma G5882) was then added and the incubation rolled at room temperature for 3 hours.

Conjugate is ready to use without purification.

Plate Coating

T3-gelatin conjugates were coated onto white microtiter wells (Dynatech, Billingshurst, UK) at a dilution of 1/750 in 100 mM Tris buffer, pH 8.0 containing 10 mg FCF blue/liter, for 20 hours at 20° C.

The wells were washed using 100mM Tris, pH 8.2, containing 0.45% NaCl and 0.05% Triton X-100.

After washing and drying plates were stored at 2-8° C.

αT4-HRP Conjugate

Polyclonal anti T4 (produced in sheep using T4-BSA as immunogen) with an affinity of $>5 \times 10^{10}$ L/mole was conjugated to HRP as follows:

0.25 ml (of a 10 mg/ml solution of HRP in 20 mM phosphate buffer, pH 7.0) was mixed with 0.2 ml sodium periodate (7mg/ml solution in same phosphate buffer) for 0.5 hour at 20° C.

20μl ethylene glycol was added to the reaction mixture and activated HRP purified in Sephadex G25 (PD10) eluted with 50mM carbonate bicarbonate buffer, pH 9.5 containing 0.1M sodium chloride.

Activated enzyme was mixed with 0.5mg (freeze-dried) polyclonal anti T4 for 2 hours at 20° C. After the addition of 50 μl NaBH4 (5 mg/ml in H2O) conjugate was mixed for 10 minutes. 0.5ml NaH2PO4 (7.8g/100 ml) was added and conjugate purified on Sephacryl S-200 eluted with 50mM phosphate, pH 7.2 (±0.3M NaCl).

The first major peak of protein was collected (total 20 ml).

Assay

To coated wells is added 25 μl human serum fT$_4$ standard and 100 μl αT$_4$ HRP dilution (1/200 of above) in phosphate buffer, 0.15M pH 7.4 containing 0.003% gelatin.

After 30 minutes incubation, plates are washed and the peroxidase bound to the surface of the wells is detected using an enhanced luminescence reaction described in European Patent Specification 87,959 using signal reagents and a luminometer available under the trade name Amerlite from Amersham International plc, U.K.

Results

| | Light Units | |
| --- | --- | --- |
| fT$_4$ | Polyclonal | Monoclonal (similar method) |
| 0 | 6845 | 13435 |
| 6.6 | 2527 | 4767 |
| 16.9 | 1281 | 1548 |
| 33.8 | 765 | 593 |
| 50.6 | 474 | 305 |
| 69.0 | 410 | 198 |

We claim:

1. A method of assaying the free portion of a ligand selected from the group consisting of thyroid hormones, steroids and cortisol, in a biological fluid sample which also contains a portion of the ligand bound to one or more natural binders, by the user of an antibody for the ligand which antibody is labeled and a differential-binding ligand analogue which competes with the ligand for binding to the antibody, which method comprises incubating the sample with the analogue and the antibody, and observing the extent of binding of the antibody to the analogue, wherein the analogue is chosen to have a binding affinity with the antibody of from 0.01% to 10% of the binding affinity of the free ligand with the antibody.

2. The method as claimed in claim 1, wherein the differential-binding ligand analogue is insolubilized prior to the incubation.

3. The method as claimed in claim 2, wherein the differential-binding ligand analogue is insolubilized by being covalently bound to cellulose or polystyrene particles.

4. The method as claimed in claim 1, wherein the antibody is labelled with I-125.

5. The method as claimed in claim 1, wherein the ratio a): b) is between 0.1 and 10, where a) is the affinity constant of the antibody for the analogue times the effective concentration of the analogue, and b) is (the affinity constant of the antibody for the ligand times the concentration of ligand bound to antibody at the end of the incubation.

6. The method as claimed in claim 1, wherein the ratio of the effective analogue concentration to the antibody concentration is from 10 to $10^5$.

7. The method as claimed in claim 1, wherein the concentration of analogue binding sites for antibody, and the free ligand concentration, are substantially the same at the beginning and end of the incubation.

8. The method as claimed in claim 1, wherein the ligand is thyroxxine and the differential-binding ligand analogue is tri-iodothyronine.

9. The method as claimed in claim 1, wherein the antibody is a monoclonal antibody to the ligand.

* * * * *

UNITED STATES PATENT AND TRADEMARK OFFICE
CERTIFICATE OF CORRECTION

PATENT NO.  : 5,278,080
DATED       : January 11, 1994
INVENTOR(S) : John Edward MIDGLEY ET AL.

It is certified that error appears in the above-identified patent and that said Letters Patent is hereby corrected as shown below:

On the Title Page:

[73] Assignee:  "Amersham International PLC,
                Buckinghamshire, Great Britain"

to

[73] Assignee:  --Amerlite Diagnostics Limited,
                Buckinghamshire, United Kingdom--.

Signed and Sealed this

Second Day of August, 1994

Attest:

BRUCE LEHMAN

*Attesting Officer*   Commissioner of Patents and Trademarks